(12) United States Patent
Oro et al.

(10) Patent No.: US 9,333,209 B2
(45) Date of Patent: May 10, 2016

(54) COMPOSITIONS FOR INCREASING HAIR GROWTH

(71) Applicant: The Board of Trustees of the Leland Stanford Junior University, Palo Alto, CA (US)

(72) Inventors: Anthony Oro, Stanford, CA (US); Ricardo Ei Dolmetsch, Stanford, CA (US); Gozde Yucel, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 14/376,595

(22) PCT Filed: Feb. 8, 2013

(86) PCT No.: PCT/US2013/025386
§ 371 (c)(1),
(2) Date: Aug. 4, 2014

(87) PCT Pub. No.: WO2013/119984
PCT Pub. Date: Aug. 15, 2013

(65) Prior Publication Data
US 2015/0005291 A1    Jan. 1, 2015

Related U.S. Application Data

(60) Provisional application No. 61/597,660, filed on Feb. 10, 2012.

(51) Int. Cl.
| | | |
|---|---|---|
| *A61P 17/14* | (2006.01) |
| *A61K 38/17* | (2006.01) |
| *A61K 31/554* | (2006.01) |
| *A61K 8/41* | (2006.01) |
| *A61K 8/49* | (2006.01) |
| *A61Q 7/00* | (2006.01) |
| *A61K 31/277* | (2006.01) |
| *A61K 31/4422* | (2006.01) |

(52) U.S. Cl.
CPC ............... *A61K 31/554* (2013.01); *A61K 8/41* (2013.01); *A61K 8/49* (2013.01); *A61K 8/4926* (2013.01); *A61K 31/277* (2013.01); *A61K 31/4422* (2013.01); *A61Q 7/00* (2013.01)

(58) Field of Classification Search
None
See application file for complete search history.

(56) References Cited

U.S. PATENT DOCUMENTS

| 2002/0035046 A1* | 3/2002 | Lukenbach et al. | 510/122 |
| 2003/0180246 A1* | 9/2003 | Frantz | A61K 8/044 424/70.21 |
| 2007/0086972 A1 | 4/2007 | Birnbaum | |
| 2008/0064765 A1 | 3/2008 | Birnbaum | |
| 2008/0267899 A1 | 10/2008 | Leskaj | |
| 2009/0258846 A1* | 10/2009 | Apple | 514/171 |

FOREIGN PATENT DOCUMENTS

| EP | 1060732 A2 | 12/2000 |
| WO | 2011109711 A | 9/2011 |

OTHER PUBLICATIONS

Horsley; et al., "NFATc1 balances quiescence and proliferation of skin stem cells", Cell (Jan. 2008), 13(2):299-310.
Oro, "A New Role for an Old Friend: NFAT and Steam Cell Quiescence", Cell Stem Cell (Feb. 2008), 2(2):104-6.
Osborne; et al., "Skin Penetration Enhancers Cited in the Technical Literature", Pharmaceutical Technology (Nov. 1997), 21:58-66.

* cited by examiner

*Primary Examiner* — H. Sarah Park
(74) *Attorney, Agent, or Firm* — Pamela J. Sherwood; Bozicevic, Field & Francis LLP

(57) ABSTRACT

Cosmetic skin and hair care compositions for enhancing the growth and appearance of mammalian hair in an individual are provided, which compositions comprise a dose of an L-type calcium channel blocker effective to promote anagen phase of the hair cycle. As shown herein, anagen phase promotion can result in more rapid hair growth.

6 Claims, 8 Drawing Sheets

COMPOSITIONS FOR INCREASING HAIR GROWTH

STATEMENT REGARDING GOVERNMENT RIGHTS

This invention was made with Government support under contract AR054780 awarded by the National Institutes of Health. The Government has certain rights in this invention.

BACKGROUND OF THE INVENTION

Adult stem cells are multipotent cells capable of executing specific differentiation programs in response to injury or key environmental signals. Many if not all adult organs possess a small number of stem cells, providing the promise of the ability to regenerate organs that are lost through injury or disease. In many tissues, multipotent stem cells are found within specific tissue niches of support cells. These niches contain specific extrinsic and intrinsic cues and act to provide regulatory signals that help pattern tissue self-renewal, proliferation or differentiation. While the relationship between stem cells and niches are known, the controls that regulate the interactions between the cells are an area of active investigation.

The hair follicle is an excellent system to study adult stem cells because of its cycle dependency and relatively short switches between growth and destruction phases. Hair follicles have two parts; one part is a permanent part that has sebaceous glands and the stem cell containing, or bulge, region. The lower or dynamic part goes through genetically controlled cycles of active growth (anagen), destruction phase (catagen) and resting phase (telogen). The timing of each of the cycle phases is exquisitely controlled and varies with environmental controls such as day length and temperature or internal controls such as metabolic or hormone status. During the resting or telogen phase, stem cells are quiescent and remain non-proliferative until the start of the next growth or anagen phase, up to three weeks later in the mouse.

The hair follicle is a complex organ composed of seven differentiation-specific tissue layers including the outer root sheath (ORS), inner root sheath (IRS) and hair shaft (HS). Hair follicle stem cells reside in the bulge region, below the sebaceous gland, in the permanent portion of the hair follicle. It has been proposed that in early anagen phase a signal from dermal papilla activates stem cells in the bulge. This causes proliferation of these cells and subsequently causes downgrowth. As the dermal papilla moves away from the bulge, the stem cells in the bulge return to their quiescent state. Stem cells in the bulge region can also give rise to epidermis in a wounding injury. Investigations over the past decade have elucidated the major signaling regulators controlling the hair cycle, where two of the central pathways for stimulating anagen are the Wnt and Shh pathways.

Hair follicle stem cells are of interest for cosmetic, as well as therapeutic, purposes. For example, androgenic alopecia is the single largest type of recognizable alopecia to affect both men and women, primarily of Caucasian origin. Androgenic alopecia or common baldness represents 99 percent of all cases of hair loss. The condition is characterized by the gradual conversion of terminal hair to short, wispy, colorless vellus hair.

It is generally accepted that genetic hair loss arises from an inherited predisposition activated by circulating androgenic hormones. While many investigators have tried to isolate the causative androgen metabolite, no single molecule has emerged. For example, in comparative studies between non-balding controls, no significant difference between mean hormonal values or amounts has been detected. This suggests that a sensitivity or receptivity to hormones at the cell binding sites within the dermal papilla is a possible factor.

In 1980, the reversal of androgenic alopecia in a male patient receiving minoxidil for hypertension was revealed and minoxidil has since been used to promote hair growth, most commonly by topical application. Minoxidil's vasodilating effect on the scalp is one of the proposed mechanisms by which minoxidil promotes hair growth. However, despite its popularity, minoxidil has not performed in a completely satisfactory fashion in promoting hair growth in all target populations. While minoxidil has been shown to stimulate some hair growth at the apex region of the scalp, hair growth at the frontal region of the scalp, for the most part, has not been shown to be improved by minoxidil treatment alone.

There is a continuing desire to treat hair loss. The present invention addresses this need.

SUMMARY OF THE INVENTION

The present invention provides cosmetic skin and hair care compositions for enhancing the growth and appearance of mammalian hair in an individual, particularly hair of the scalp. In some embodiments of the invention the cosmetic formulations are topical formulations that comprise a dose of an L-type calcium channel blocker effective to promote anagen phase of the hair cycle. Alternatively a protein acting downstream of Cav 1.2 is administered, for example follistatin-like protein 1 (FSTI1), is administered to promote anagen phase of the hair cycle. As shown herein, anagen phase promotion can result in more rapid hair growth. In some embodiments, the L-type calcium channel blocker is selected from nifedipin, verapamil and diltiazem. The formulations of the invention may further include cosmetically acceptable vehicle(s) and/or other skin and hair conditioning agents. Additional agents to enhance skin penetration may be included in the formulation.

In the methods of the invention, a topical composition comprising an effective dose of an L-type calcium channel blocker or a downstream protein is administered to the scalp of an individual for a period of time sufficient to improve the appearance of the individual's hair. The individual may be a human suffering from androgenic alopecia. In some embodiments a topical composition comprising an effective dose of an L-type calcium channel blocker is administered to the eyebrows or eyelashes of an individual for a period of time sufficient to improve the appearance of the eyebrows or eyelashes.

In some embodiments, methods are provided for screening an agent having hair growth promoting activity, comprising the step of: bringing a hair follicle into contact with a test agent, and judging that the agent tested is positive when the hair follicle is led to anagen phase by the agent tested, and wherein the judgment is carried out by detecting calcium levels in the hair follicle. When compared, calcium levels are lower in anagen phase and higher in telogen phase.

These and other objects, advantages, and features of the invention will become apparent to those persons skilled in the art upon reading the details of the treatment methods, and in vitro and in vivo assay methods, as more fully described below.

DEFINITIONS

Figure 1:
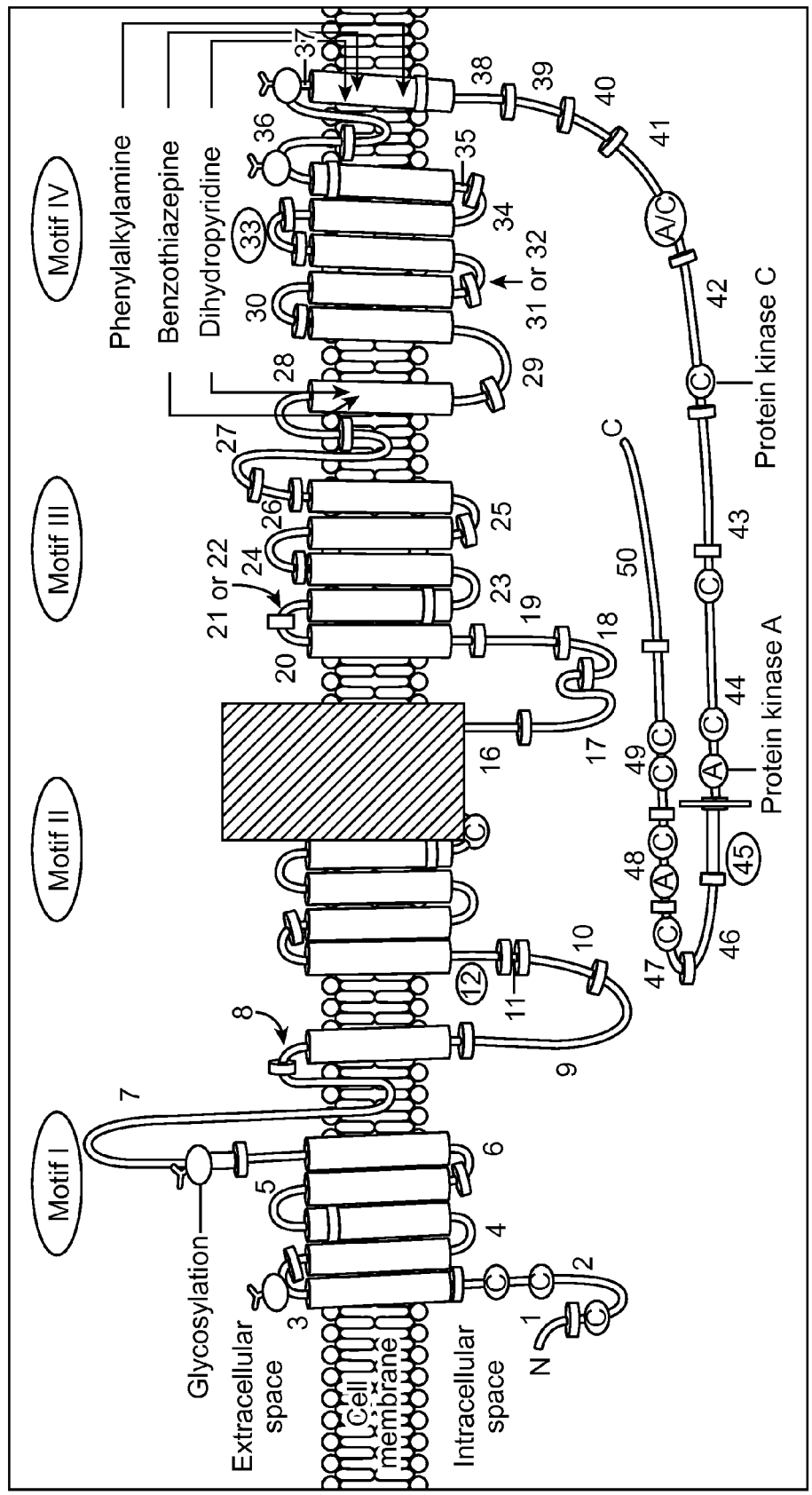
FIG. 1. Cav 1.2 knock out strategy

"Mammalian hair," as used herein, includes hair on any part of the body of a mammal and may include facial, cranial, or body hair. Of particular interest for increased hair growth is the hair present on the human scalp. Hair of the eyelashes and eyebrows is also of interest for growth modification with the methods of the invention.

"Regulating hair growth," namely mammalian hair growth, includes reducing, modulating, inhibiting, attenuating, retarding, promoting, enhancing, and/or the diminution of hair growth, and/or reducing shaving frequency. Enhancement or promotion of hair growth is of particular interest.

"Promoting hair growth" includes stimulating an increase in total hair mass and/or length. Such increase includes increased length and/or growth rate of hair shafts (i.e. follicles), increased number of hairs, and/or increased hair thickness. Some or all of the above end results can be achieved by prolonging or activating anagen, the growth phase of the hair cycle, or by shortening or delaying the catagen and telogen phases. "Promoting hair growth" should also be considered to include preventing, arresting, decreasing, delaying and/or reversing hair loss.

"Anagen," as used herein, refers to the active growth phase of hair follicles. In the anagen phase, cells in the root of the hair divide rapidly, adding to the hair shaft. During this phase, the hair grows about 1 cm every 28 days. Scalp hair stays in this active phase of growth for 2-6 years.

"Catagen," as used herein, refers to the hair growth phase that occurs at the end of the anagen phase. It signals the end of the active growth of a hair. This phase lasts for about 2-3 weeks while a club hair is formed.

"Telogen," as used herein, refers to the resting phase of the hair follicle. At any given time, 10%-15% of all hairs are in the telogen phase. This phase lasts for about 100 days for hairs on the scalp and much longer for hairs on the eyebrows, eyelashes, arms and legs. During this phase, the hair follicle is completely at rest and the club hair is completely formed. Pulling out a hair in this phase will reveal a solid, hard, dry, white material at the root. About 25-100 telogen hairs are shed normally each day.

A "growth state" of a cell refers to the rate of proliferation of the cell and/or the state of differentiation of the cell.

An "active agent" is an agent, drug, compound, or composition of matter or mixture thereof which provides some pharmacologic, often beneficial, effect.

"Topical application" or "topical," as used herein, means to apply or spread the compositions of the present invention onto the surface of a keratinous tissue.

"Dermatologically-acceptable," as used herein, means that the compositions or components thereof so described are suitable for use in contact with mammalian keratinous tissue without undue toxicity, incompatibility, instability, allergic response, and the like.

"Safe and effective amount" as used herein, means an amount of a compound or composition sufficient to significantly induce a positive benefit, preferably a hair growth regulating benefit, or positive hair appearance or feel benefit, including independently or in combinations the benefits disclosed herein, but low enough to avoid serious side effects, i.e., to provide a reasonable benefit to risk ratio, within the scope of sound judgment of the skilled artisan.

DETAILED DESCRIPTION OF THE EMBODIMENTS

The present invention provides cosmetic skin and hair care compositions for enhancing the growth and appearance of mammalian hair in an individual, particularly hair of the scalp. In some embodiments of the invention the cosmetic formulations are topical formulations. In some embodiments the cosmetic formulations comprise a dose of an L-type calcium channel blocker effective to promote anagen phase of the hair cycle, resulting in more rapid hair growth. In some embodiments, the L-type calcium channel blocker is selected from nifedipin, verapamil and diltiazem. The hair care compositions of the invention contain active ingredients that provide for thicker, longer and more voluminous appearing hair. The formulations of the invention may further include cosmetically acceptable vehicle(s) and/or other skin and hair conditioning agents. Additional agents to enhance skin penetration may be included in the formulation.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Compositions are provided for enhancing the growth of hair, where the composition comprises an L-type calcium channel blocker at a dose effective to promote mammalian hair growth. In some embodiments the formulation is a topical formulation. Topical formulations are administered to the region of skin comprising hair follicles, particularly skin of the scalp, but in some embodiments also comprising the skin of the eyelashes, eyebrows, beard, etc. The individual being treated may be male or female, usually a mammal, and usually a human. The individual may suffer from a hair loss condition, such as androgenic alopecia, or from alopecia resulting from various other causes. Alternatively, the individual can have normal hair growth who desires to have a promotion of hair growth or regulation of hair growth.

The compositions of the present invention are for topical use and are to be applied to the regions of skin comprising hair follicles, e.g. scalp, eyebrows, eyelashes, etc. The amounts and concentrations of the active agents in the compositions of the invention will vary depending on several different factors, including but not hereby limited to, the pH and condition of the skin; whether the skin is oily, dry, or in-between and the nature of the interaction between the various other agents to be included in the composition, but should be such to be effective while at the same time reducing the risk of untoward side effects, such as inflammation and unwanted change in the pigmentation of the hair or skin. Optimization of the concentration of the active agent(s), suitable for use with different skin types, which are used within the compositions of the invention, can be routinely determined by a skilled worker using well known methods that are commonly practiced within the art.

Calcium Channels and L-Type Calcium Channels

The formulations of the invention can comprise a dose of an L-type calcium channel blocker effective to promote anagen phase of the hair cycle. Calcium channels are membrane-spanning, multi-subunit proteins that allow controlled entry of $Ca^{2+}$ ions into cells from the extracellular fluid. Cells throughout the animal kingdom, and at least some bacterial, fungal and plant cells, possess one or more types of calcium channel.

The most common type of calcium channel is voltage dependent. All "excitable" cells in animals, such as neurons of the central nervous system (CNS), peripheral nerve cells and muscle cells, including those of skeletal muscles, cardiac muscles, and venous and arterial smooth muscles, have voltage-dependent calcium channels. "Opening" of a voltage-dependent channel to allow an influx of $Ca^{2+}$ ions into the cells requires a depolarization to a certain level of the potential difference between the inside of the cell bearing the channel and the extracellular environment bathing the cell. The rate of influx of $Ca^{2+}$ into the cell depends on this potential difference.

Multiple types of calcium channels have been identified in mammalian cells from various tissues, including skeletal muscle, cardiac muscle, lung, smooth muscle and brain, [see, e.g., Bean, B. P. (1989) Ann. Rev. Physiol. 51:367-384 and Hess, P. (1990) Ann. Rev. Neurosci. 56:337]. Calcium channels can be classified into a number of types and subtypes, for example L-(or $Ca_v1$), P/Q-(or $Ca_v2.1$), N-(or $Ca_v2.2$), R-($Ca_v2.3$) and T-(or $Ca_v3$) types, and are distinguished by current kinetics, holding potential sensitivity and sensitivity to calcium channel agonists and antagonists. The structural form of voltage-dependent calcium channels are a complex of several different subunits: $\alpha_1, \alpha_2\delta, \beta_{1-4}$) and $\gamma$. The $\alpha_1$ subunit forms the ion conducting pore while the associated subunits have several functions including modulation of gating.

An L-type calcium channel (or $Ca_v1$) is also known as a "long lasting" or "DHP receptor." L-type calcium channel can be further characterized as $Ca_v1.1$, $Ca_v1.2$, $Ca_v1.3$, and $Ca_v1.4$.

Calcium channel, voltage-dependent, L type, α1C subunit (also known as $Ca_v1.2$) is a subunit of L-type voltage-dependent calcium channel encoded by the CACNA1C gene, mutation in which are associated with a variant of Long QT syndrome called Timothy's syndrome and also with Brugada syndrome.

L-Type Calcium Channel Blockers

A number of compounds are thought to exert their effects by modulating functions of voltage-dependent calcium channels. Many of these compounds bind to calcium channels and block, or reduce the rate of, influx of $Ca^{2+}$ into the cells in response to depolarization of the cell membrane.

As used herein, "calcium channel blocker" is intended to embrace one or more compounds or agents having the ability to interact with and block calcium transport through calcium channels located on various human body tissues which are associated with mediating one or more biological functions or events.

In some embodiments, the calcium channel blocker exhibits $IC_{50}$ values of about 1 µM or less. In some embodiments, the calcium channel blocker exhibits $IC_{50}$ values of about 0.9 µM, 0.8 µM, 0.7 µM, 0.6 µM, 0.5 µM, 0.4 µM, 0.3 µM, 0.2 µM, or 0.1 µM or less. The $IC_{50}$ is the concentration which inhibits 50% of the calcium, barium or other permeant divalent cation flux at a particular applied potential, e.g. +10 mV. In some embodiments, the composition comprises an L-type calcium channel blocker that interacts with or blocks calcium transport through a $Ca_v1.2$.

One class of L-type calcium channel blocker includes dihydropyridines. Dihydropyridines include, but are not limited to, amlodipine, aranidipine, azelnidipine, barnidipine, benidipine, cilnidipine, clevidipine, efonidipine, felodipine, isradipine, lacidipine, lercanidipine, manidipine, nicardipine, nifedipine, nilvadipine, nimodipine, nisoldipine, nitrendipine, and pranidipine. A particular L-type calcium channel blocker of interest is nifedipine.

Another class of L-type calcium channel blocker includes phenylalkylamines. Phenylalkylamines include, but are not limited to, verapamil and gallopamil. A particular L-type calcium channel blocker of interest is verapamil.

Another class of L-type calcium channel blocker includes benzothiazepines. Benzothiazepines include, but are not limited to, diltiazem, which is of particular interest.

Follistatin-Like 1 Protein

As demonstrated herein, administration of Follistatin-like 1 protein, FSTL1, also promotes anagen. A protein composition may be used in the methods of the invention as an alternative or in addition to the L-type calcium channel blockers. The effective dose of the protein may be determined empirically, e.g. from about 1 ng to 100 mg per dose, as formulated appropriately for the condition to be treated.

FSTL1 encodes a deduced 308-amino acid protein with an N-terminal signal peptide of 20 amino acids. FSTL1 contains an FS module, a follistatin-like sequence containing 10 conserved cysteine residues. The number and distribution of the cysteine residues supports the existence of several intramolecular disulfide bridges. The sequence of the protein is known in the art, under the HGNC approved symbol FSTL1, and as described by Zwijsen et al. (1994) Europ. J. Biochem. 225: 937-946.

For topical formulations, the FSTL1 protein may be provided with a penetration enhancer, e.g. DMSO, etc.

Formulations Comprising Active Agent

According to the present invention "formulation" is a generic term which can encompass additives, personal care, cosmetic, and dermopharmaceutical compositions, and additives and personal care, cosmetic, and dermopharmaceutical compositions. Formulations can also cover additives and personal care, cosmetic and dermopharmaceutical compositions comprising an active agent.

In general, the subject formulations will typically contain at least about 1 µg/ml active agent, at least about 10 µg/ml, at least about 50 µg/ml, at least about 100 µg/ml, at least about 500 µg/ml, and not more than about 50 mg/ml, usually not more than about 10 mg/ml. In some embodiments the formulation comprises at least about 0.1 mM, at least about 0.05, at least about 1 mM, at least about 5 mM, at least about 10 mM, at least about 50 mM, and not more than about 500 mM, not more than about 250 mM active agent. The active agents of the present invention are formulated at an effective concentration within the subject formulations, meaning at a concentration that provides the intended benefit when applied topically. In certain embodiments, the active agent is an L-type calcium channel blocker.

The L-type calcium channel blocker can be effective to promote anagen phase of the hair cycle, resulting in more rapid hair growth. The L-type calcium channel blocker can be used for conditions in which regulating hair growth or promoting hair growth is desired. The compositions of the invention are used for the topical treatment of a hair loss condition, such as alopecia in a mammal. The individual being treated may be a human, or may be an animal, e.g. canine, equine, bovine, etc. suffering from hair loss. In other embodiments the individual is a laboratory animal, e.g. rabbit, mouse, rat, etc., for purposes of evaluating treatments.

An L-type calcium channel blocker may be combined with any additional ingredient which may be active, functional, conventionally used in cosmetic, personal care or topical/transdermal pharmaceutical products or otherwise. Of course, a decision to include an additional ingredient and the choice of specific additional ingredients depends on the specific application and product formulation. Also, the line of demarcation between an "active" ingredient and an "inactive" ingredient" is artificial and dependent on the specific application and product type. A substance that is an "active" ingredient in one application or product may be a "functional" ingredient in another, and vice versa.

In order to be effective in stimulating hair growth the composition may be formulated in such a way as to enhance the active agent's penetration of the skin. Accordingly, the composition may be formulated in conjunction with a skin penetration enhancing agent so as to better enable the active agent to deeply penetrate the epidermis of the skin. The formulations can include other components, such as buffering agents, lipophilic agents and cosmetically acceptable vehicles. These components are explained in more detail below.

In certain embodiments, a composition of the invention includes as an active agent an L-type calcium channel blocker in a synergistic combination with at least one skin penetration enhancing agent, and which may also include a suitable buffering agent.

The formulations may be used in the form of solutions, dispersions and emulsions, or may comprise carriers such as macrocapsules, microcapsules, nanocapsules, macrospheres, microspheres, nanospheres, liposomes, oleosomes, chylomicrons, macroparticles, microparticles, nanoparticles, macrosponges, microsponges, nanosponges, powdered organic polymers, talcs, bentonites or other inorganic carriers.

The formulations may be used in any form employed in cosmetics or dermopharmacy: such as lotions, shampoos, conditioners, hair sprays, gels, hair styling products, hair holding products, sunscreens, sunblocks, soaps, creams, emulsions, dispersions, solutions, milks, suspensions, cleansers, washes, scalp treatment lotions, or sprays.

Skin Penetration Enhancing Agent

As used herein, a skin penetration enhancing agent is any factor that increases the penetration of the skin, preferably with minimal disruption to the acidic pH balance of the skin. Preferably, the skin penetration enhancing agent enhances the percutaneous delivery of the active agent into and through the layers of the skin, without providing substantial transdermal transmission of the active agent into the systemic circulation. The permeability enhancing agents of the invention are physio-chemically stable, do not have pharmacological effects, and have at least reduced irritancy or toxicity to the skin. When present in a composition of the invention, the amount of penetration enhancer is typically from about 1% to about 10% by weight of the total composition weight or from about 2% to about 5% by weight. The formulation and use of skin penetration enhancers in topical formulations is set forth generally in: PERCUTANEOUS PENETRATION ENHANCERS (Eric W. Smith & Howard I. Maibach eds. 1995); Ghosh, T. K. et al. 17 PHARM. TECH. 72 (1993); Ghosh, T. K. et al. 17 PHARM. TECH. 62 (1993); and Ghosh, T. K. et al. 17 PHARM. TECH. 68 (1993), all of which are hereby incorporated herein by reference in their entirety.

Suitable skin penetration enhancing agents include those agents that are capable of reducing the resistance of the skin to the active agent and promoting the active agent partitioning from the dosage form. Penetration enhancing agents may function in a variety of ways, including via the elution of the lipid and/or lipoprotein structures of the stratum corneum, by increasing lipid fluidity (e.g., by disrupting the tightly packed lipid chains), or by engaging in various protein interactions that result in a change in protein and/or lipid configuration that creates a passage for the active agent. Suitable topical skin permeability enhancing agents can be routinely selected for a particular use by those skilled in the art, and especially with reference to one of many standard texts in the art, such as Remington's Pharmaceutical Sciences, Vol. 18, Mack Publishing Co., Easton, Pa. (1990), in particular Chapter 87, which is hereby incorporated by reference in its entirety.

Accordingly, suitable skin penetration enhancing agents include but are not hereby limited to: sulfoxides, alcohols, polyols, fatty acids, esters, amides, surface active agents (such as pluronics, sulfates, lecithin, docusate sodium, polysorbates), water, and the like. Specifically, skin penetration enhancing agents include but are not hereby limited to dimethyl sulfoxide (DMSO), N-decylmethylsulfoxide, ethanol, phenyl ethanol, propylene glycol, lauric or myristic or palmitic or steric fatty acids, lauric acid, sodium laurate, neodecanoic acid, lauryl lactate, methyl laurate, hexamethylene lauramide, leucinic acid, oleic acid, capric acid, sodium oleate, sodium caprate, dodecyl-amine, cetryl lactate, myristyl lactate, isopropyl palmitate or isopropyl myristate esters, urea and derivatives, dodecyl N,N-dimethylamino acetate, hydroxyethyl lactamide, lecithin, phyophatidylcholine, sefsol-318 (a medium chain glyceride, surfactants, including polyoxyethylene (10) lauryl ether (Brij 361 R), diethyleneglycol lauryl ether (PEG-2-L), laurocapram (Azone; 1,1-dodecylazacycloheptan-2-one), acetonitrile, 1-decanol, 2-pyrrolidone, N-methylpyrrolidone, N-ethyl-1-pyrrolidone, 1-methyl-2-pyrrolidone, 1-lauryl-2-pyrrolidone, sucrose monooleate, acetone, polyethylene glycol 100-400 MW, dimethylacetamide, dimethylforamide, dimethylisosorbide, sodium bicarbonate, mentane, menthone, menthol, terpinene, D-terpinene, dipentene, N-nonalol, limonene, and various $C_{7-16}$-alkanes in amounts that are safe and effective.

A vasodilator that can be used in the formulations of the present invention is niacinamide (a vitamin $B_3$ compound), which aids in the penetration and uptake of active ingredients. The niacinamide may be used at a concentration of at least about 0.25% to 0.5%, more usually at least about 1%, and not more than about 5%.

Buffering Agents

The normal pH of the skin is between about 4 and about 6.5, though it varies in people of different skin types. The compositions of the invention, therefore, in certain embodiments, should be formulated in such a manner so as to reduce the effects that the actual application of the composition has on the pH barrier of the skin and/or should be formulated in a manner so as to increase the penetration of the active agent. Accordingly, in certain embodiments the typical pH ranges for the compositions of the invention include a pH of about 3 to about 8, of about 4 to about 7, and more typically about 4.5 to about 6.5 or about 5. The desired pH ranges of the compositions of the invention can be obtained in accordance with practices well known in the art, for instance, by the inclusion of various buffering agents, which should be included in an amount and concentration to optimize the flux of the active agent through the skin surface and into the dermal layer of skin, while minimizing any possibility of skin irritation due to a change in the pH of the skin.

A conventional buffering agent such as a mixture of citric acid and trisodium citrate, may be added to stabilize the desired pH. Other buffering agents include, but are not limited to, sodium phosphate, monosodium dihydrogen phosphate, and disodium monohydrogen phosphate.

Lipophilic Agents

Various lipophilic agents may also be included as cosmetic benefit agents of the present invention in amounts that are safe and effective. A lipophilic agent to be added to a composition of the invention may be, for instance, a water-insoluble (hydrophobic) organic material or mixture of materials that are miscible with an L-type calcium channel blocker and are suitable for topical administration and formulated to enhance the penetration of an active agent of the invention. A lipophilic component may be in a range about 15% to about 40% by weight of the total composition weight or about 20% by weight.

Suitable lipophilic components are well known in the art and include, but are not limited to, vegetable, nut, and seed oils, such as almond oil, castor oil, coconut oil, corn oil, cotton seed oil, jojoba oil, linseed oil, grape seed oil, rape seed oil, mustard oil, olive oil, palm and palm kernel oil, peanut oil, safflower oil, sesame oil, soybean oil, sunflower-seed oil, crambe oil, wheat germ oil, and cocoa butter; animal oils and fats, such as lanolin, tallow, lard, beef fat, butterfat, mink oil, and fish oils; hydrocarbon and petroleum oils, such as petrolatum, mineral oil, and liquid paraffin. Additional lipophilic components include higher fatty acids such as lauric acid, myristic acid, palmitic acid, stearic acid, behenic acid, oleic acid, 12-hydroxystearic acid, undecylenic acid, tall acid, lanolin fatty acid, isostearic acid, linoleic acid and linolenic acid.

The lipophilic component may also include a suitable stiffening agent such as isopropyl myristate, glycerol monolaurate, glycerol monooleate, glycerol monolinoleate, isopropyl isostearate, isopropyl linoleate, isopropyl myristate/fatty acid monoglyceride combination, isopropyl myristate/ethanol/L-lactic acid combination, isopropyl palmitate, methyl acetate, methyl caprate or methyl laurate.

The formulation may also contain irritation-mitigating additives to minimize or eliminate the possibility of skin irritation or skin damage that may result from the penetration of the active agent or other components of the formulation. Suitable irritation-mitigating additives include, for example: α-tocopherol; monoamine oxidase blockers, particularly phenyl alcohols, such as 2-phenyl-1-ethanol; glycerin; salicylic acids and salicylates; ascorbic acids and ascorbates; ionophores such as monensin; amphiphilic amines; ammonium chloride; N-acetylcysteine; cis-urocanic acid; capsaicin; and chloroquine. The irritant-mitigating additive, if present, may be incorporated into the formulation at a concentration effective to mitigate irritation or skin damage, typically representing not more than about 20 wt %, more typically not more than about 5 wt %, of the formulation.

Cosmetically Acceptable Vehicle

The formulation can comprise a cosmetically acceptable vehicle to act as a dilutant, dispersant or carrier for an active agent of the invention, so as to facilitate its distribution and uptake when the composition is applied to the skin and/or hair or scalp. Vehicles other than or in addition to water can include liquid or solid emollients, solvents, humectants, thickeners and powders.

The cosmetically acceptable vehicle will usually form from about 5% to about 99.9%, preferably from about 25% to about 80% by weight of the composition, and can, in the absence of other cosmetic adjuncts, form the balance of the composition.

The compositions may be in the form of aqueous, aqueous/alcoholic or oily solutions; dispersions of the lotion or serum type; anhydrous or lipophilic gels; emulsions of liquid or semi-liquid consistency, which are obtained by dispersion of a fatty phase in an aqueous phase (O/W) or conversely (W/O); or suspensions or emulsions of smooth, semi-solid or solid consistency of the cream or gel type. These compositions are formulated according to the usual techniques as are well known to this art.

A topical cosmetic composition of the invention will typically be formulated as a lotion which is prepared to be applied to the skin surface without friction, and which is typically a liquid or semiliquid preparation in which the active agent(s) of the invention are present in a lipid, alcohol or water base. Lotions are usually suspensions of solids, and typically, for the present purpose, comprise a liquid oily emulsion of the oil-in-water type. Lotions are typical formulations herein for treating the facial and scalp areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethyl-cellulose, or the like.

Solutions are, typically, homogeneous mixtures prepared by dissolving one or more chemical substances (solute) in another liquid such that the molecules of the dissolved substance are dispersed among those of the solvent. The solution may contain other cosmetically acceptable chemicals to buffer, stabilize or preserve the solute. Commonly used examples of solvents used in preparing solutions are ethanol, water, propylene glycol or any other cosmetically acceptable vehicle, as for example, set forth below.

When the compositions of the invention are formulated as an oily solution or gel, the fatty phase may constitute more than about 90% of the total weight of the composition.

When the compositions of the invention are formulated as an emulsion, the proportion of the fatty phase may range from about 5% to about 80% by weight, and preferably from about 5% to about 50% by weight, relative to the total weight of the composition. Oils, emulsifiers and co-emulsifiers incorporated in the composition in emulsion form are selected from among those used conventionally in the cosmetic or dermatological field. The emulsifer and coemulsifier may be present in the composition at a proportion ranging from about 0.3% to about 30% by weight, and preferably from about 0.5% to about 20% by weight, relative to the total weight of the composition.

Exemplary oils which may be used according to this invention include mineral oils (liquid petrolatum), plant oils (liquid fraction of karite butter, sunflower oil), animal oils (perhydrosqualen(e), synthetic oils (purcellin oil), silicone oils (cyclomethicone) and fluoro oils (perfluoropolyethers). Fatty alcohols, fatty acids (stearic acid) and waxes (paraffin wax, carnauba wax and beeswax) may also be used as fats.

Emulsifiers which may be used include glyceryl stearate, polysorbate 60, PEG-6/PEG-32/glycol stearate mixture, etc. Solvents which may be used include the lower alcohols, in particular ethanol and isopropanol, and propylene glycol.

An oil or oily material may be present, together with an emollient to provide either a water-in-oil emulsion or an oil-in-water emulsion, depending largely on the average hydrophilic-lipophilic balance (HLB) of the emollient employed. Levels of such emollients may range from about 0.5% to about 50%, preferably between about 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

The compositions of the invention may also contain additives and adjuvants which are conventional in the cosmetic, pharmaceutical or dermatological field, such as hydrophilic or lipophilic gelling agents, hydrophilic or lipophilic active agents, preservatives, antioxidants, solvents, fragrances, fillers, bactericides, odor absorbers and dyestuffs or colorants. The amounts of these various additives and adjuvants are those conventionally used in the field, and, for example, range from about 0.01% to about 10% of the total weight of the composition. Depending on their nature, these additives and adjuvants may be introduced into the fatty phase or into the aqueous phase.

Another category of functional ingredients within the cosmetic compositions of the present invention are thickeners. A thickener will usually be present in amounts anywhere from about 0.1 to about 20% by weight, preferably from about 0.5% to about 10% by weight of the composition. Exemplary thickeners are cross-linked polyacrylate materials available under the trademark Carbopol. Gums may be employed such as xanthan, carrageenan, gelatin, karaya, pectin and locust beans gum. Under certain circumstances the thickening function may be accomplished by a material also serving as a silicone or emollient. For instance, silicone gums in excess of about 10 centistokes and esters such as glycerol stearate have dual functionality.

Powders may be incorporated into the cosmetic composition of the invention. These powders include chalk, talc, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct components may also be incorporated into the cosmetic compositions. These ingredients may include coloring agents, opacifiers and perfumes. Specifically, these ingredients may include cosmetically suitable additives such as deionized water, hydrolyzed glycosaminoglycan, sodium hyaluraonate, triethanolamine, propylene glycol, methylparaben, propylparaben, acrylates, C10-C20 alkyl acrylate crosspolymers, C12-C15 alkyl benzoate, panthenol, biotin, sodium chloride, sodium phosphate and the like. Amounts of these other adjunct components may range anywhere from about 0.001% up to about 20% by weight of the composition.

Product Use, Form, and Packaging

In use, a quantity of the composition, for example from about 0.0001 ml to about 100 ml, from about 0.001 ml to about 10 ml, from about 0.01 ml to about 1 ml, typically about 0.1 ml is applied to a site of interest (i.e., skin or hair of the eyelash, eyebrow, and/or scalp) from a suitable container or applicator and, if necessary, it is then spread over the site. The product may be specifically formulated for use as a treatment for a specific area, e.g. the eyelashes, eyebrows, the face, the hair, or the scalp.

The cosmetic composition of the invention can be formulated in any form suitable for application to the site of interest). The composition can be packaged in a suitable container to suit its viscosity and intended use by the consumer. For example, a gel can be packaged in a bottle or a container fitted with a fine brush suitable controlled application to the lash line or eyebrow. The invention accordingly also provides a

Therapeutic Conditions

As described herein, a dose of an L-type calcium channel blocker effective to promote anagen phase of the hair cycle, resulting in more rapid hair growth. An L-type calcium channel blocker can be used for conditions in which regulating hair growth or promoting hair growth is desired. Promoting hair growth can be performed on a subject with normal hair growth or a hair loss condition. Under normal hair growth conditions on the scalp, about 88% of the hairs are in the anagen phase, about 1% in catagen and the remainder in telogen.

A hair loss condition is alopecia. "Alopecia," as used herein is defined as loss of hair, includes, for example, alopecia areata, androgenic alopecia, etc. Hair loss is often a cause of great concern to the patient for cosmetic and psychological reasons. Hair grows in cycles. Each cycle consists of a long growing phase (anagen), a brief transitional apoptotic phase (catagen), and a short resting phase (telogen). At the end of the resting phase, the hair falls out (exogen) and a new hair starts growing in the follicle, beginning the cycle again. Normally, about 100 scalp hairs reach the end of resting phase each day and fall out. When significantly more than 100 hairs/day go into resting phase, clinical hair loss (telogen effluvium) may occur. A disruption of the growing phase causing abnormal loss of anagen hairs is an anagen effluvium. Besides the loss of hair, the length and diameter of each hair will be reduced in the adjacent areas even though the follicles remain intact.

Conditions of hair loss include alopecia areata, traction alopecia, trichotillomania, tinea capitis (fungal infection), telogen effluvium, and androgenic alopecia ("male-pattern baldness", "female-pattern baldness"). Causes of alopecia include administration of chemotherapeutic agents and radiation, which impair or disrupt the anagen cycle. Other conditions resulting in hair loss include infection, systemic illnesses (particularly those that cause high fever, systemic lupus, endocrine disorders, and nutritional deficiencies). The compositions of the present invention find use in alleviating alopecia associated with these conditions.

Telogen effluvium is a transient, reversible, diffuse shedding of hair in which a high percentage of hair follicles enter the telogen phase prematurely as a result of physical or mental illness. Among the most important factors incriminated are childbirth, high fever, hemorrhage, sudden starvation, accidental or surgical trauma, severe emotional stress, and certain drugs.

Alopecia areata is an immunologic alopecia characterized by the abrupt onset of sharply defined areas of hair loss. In the most severe cases, the scalp will develop total hair loss (alopecia totalis) or the hair loss will involve the whole body surface (alopecia universalis). Most of the patients will run an unpredictable and relapsing course with multiple episodes of hair loss and regrowth. About 20 to 30 percent will have a single reversible episode. Regrowth of hair is common within several months, but in many instances is not complete, and relapses are common. Alopecia areata may be associated with autoimmune diseases such as vitiligo, pernicious anemia, collagen disease, and endocrinopathies.

Traumatic alopecia is induced by physical trauma, of which the two most important groups, from the therapeutic standpoint are trichotillomania and alopecia resulting from cosmetic procedures or improper hair care. Trichotillomania is a compulsive habit in which the individual repeatedly pulls or breaks off his or her own hair in a partially conscious state similar to thumb sucking or nail biting. Traumatic alopecia from cosmetic procedures is done consciously in ill-advised individuals and is almost exclusively seen among females. Sometimes this type of alopecia is associated with folliculitis induced by the occlusive effect of the oily cosmetics used in the procedure.

Anagen effluvium is a temporary alopecia caused by the inhibition of mitosis in the hair papilla by certain cytotoxic drugs, leading to constriction of the hair shaft or to complete failure of hair formation. In particular, alopecia frequently occurs in cancer patients who are treated with chemotherapeutic drugs and/or irradiation. Such agents damage hair follicles which contain mitotically active hair-producing cells. Such damage may cause abnormally slow growth of the hair or may lead to hair loss. While various attempts have been made to protect against alopecia or abnormal rates of hair growth during such treatments, there remains a need for an agent that prevents damage to hair follicles in a safe and effective manner.

Alopecia may also result from nutritional deficiencies and metabolic defects. Caloric deprivation must be very severe to produce hair loss. Increased shedding sometimes occurs after marked weight loss for obesity. Anemia, diabetes, hyper- and hypovitaminosis, and zinc deficiency may also lead to alopecia.

Screening Applications

The methods of the invention induce hair follicle differentiation, inducing a shift in hair growth cycle from telogen to anagen in skin, and increasing the rate of hair shaft elongation in skin. Effective agents for use in the methods of the invention inhibit NFAT/calcineurin-promoted signal transduction in certain hair follicle cells, and may be identified by that activity.

In some embodiments, methods are provided for screening an agent having hair growth promoting activity, comprising the step of: bringing a hair follicle into contact with a test agent, and judging that the agent tested is positive when the hair follicle is led to anagen phase by the agent tested, and wherein the judgment is carried out by detecting calcium levels in the hair follicle. When compared, calcium levels are lower in anagen phase and higher in telogen phase. The screening can be performed in vitro or in vivo.

In one embodiment, after stem cells are exposed to a test agent, the effects on growth state of the stem cells can be determined using procedures and equipment, such as the assays disclosed herein. Exposure encompasses contacting the stem cells with the compound or administering the compound to a subject. The determining step can involve measuring a response (a quantitative analysis) or can involve making an observation (a qualitative analysis).

The determination of calcium levels can be done in vitro. For in vitro determination of calcium levels, stem cells can be isolated by fluorescence activated cell sorting (FACS). The calcium levels in the stem cells can be measured. Calcium levels in stem cells that are exposed to test agents can be compared to calcium levels in control stem cells that have not been exposed to test agents. Calcium levels in the stem cells are lower in anagen phase and higher in telogen phase.

EXAMPLES

The following examples are put forth so as to provide those of ordinary skill in the art with a complete disclosure and description of how to make and use the subject invention, and are not intended to limit the scope of what is regarded as the invention. Efforts have been made to insure accuracy with respect to the numbers used (e.g. amounts, temperature, concentrations, etc.) but some experimental errors and deviations should be allowed for. Unless otherwise indicated, parts are parts by weight, molecular weight is weight average molecular weight, temperature is in degrees centigrade, and pressure is at or near atmospheric.

Example 1

L-Type Calcium Channel Blocker Causes Entry to Anagen

Figure 3:
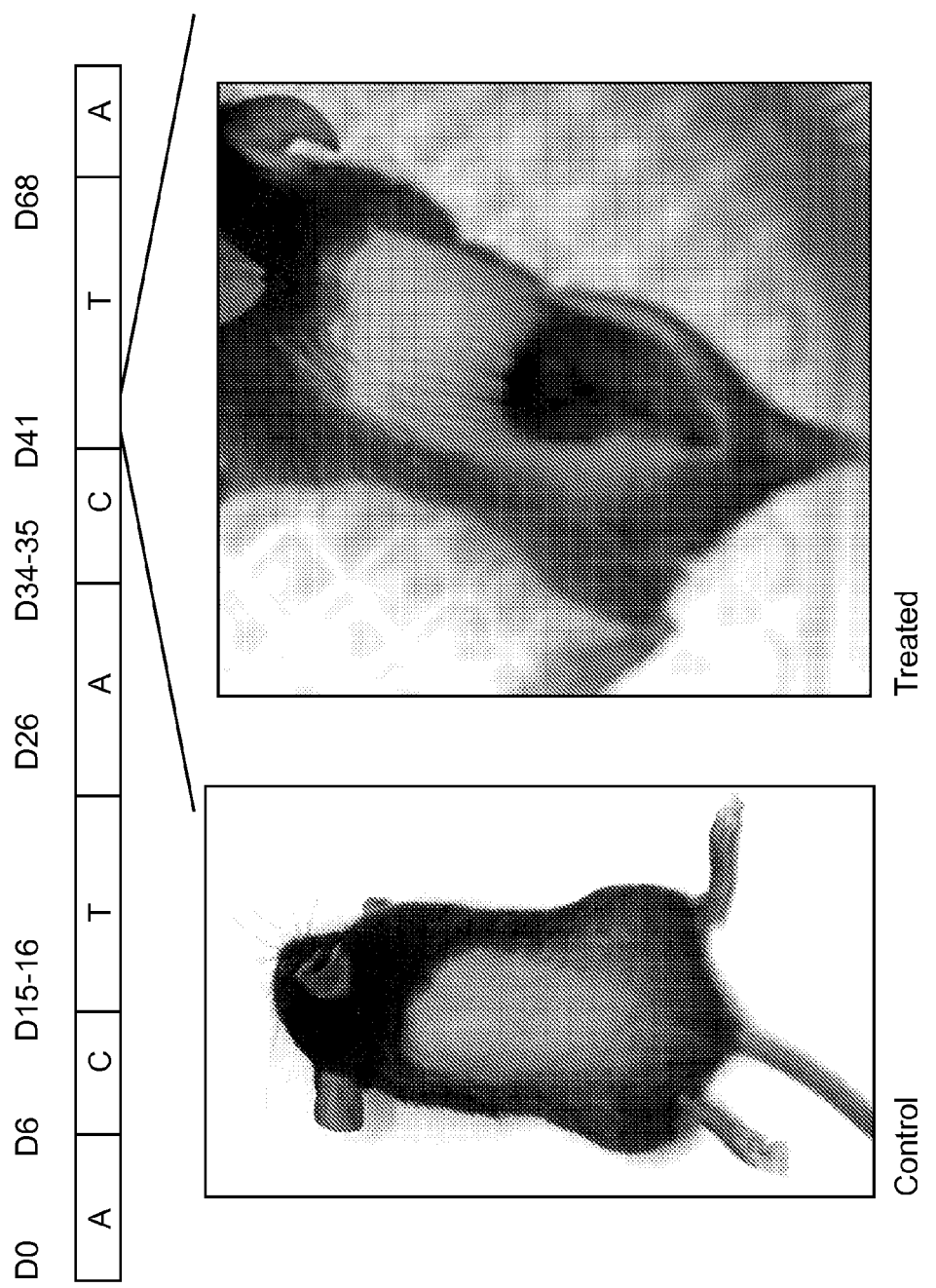
FIG. 3. Induction of Cav 1.2 knock-out.
Figure 4:
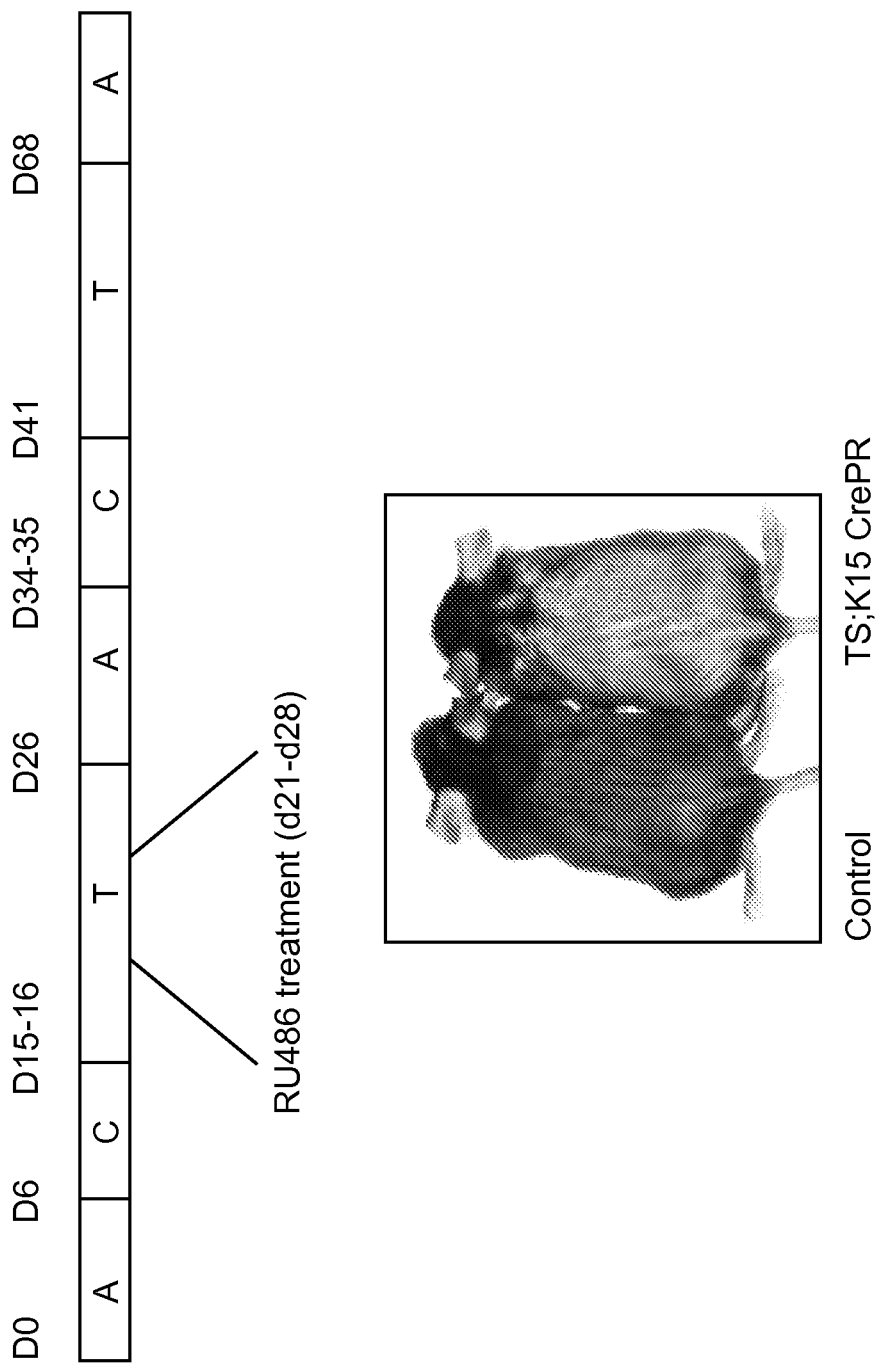
FIG. 4. Induction of TS knock-out.

To understand how calcium signaling controls hair follicle stem cell regulation, a screen for small molecules that affect murine hair follicle cycling was carried out. The compounds included a survey of different classes of cell permeable slow and fast channel blockers applied to the skin. One class of compounds, the L type voltage gated calcium channel blocker nifedipine, caused precocious entry to anagen after two weeks of topical treatment in $2^{nd}$ telogen phase, as shown in FIG. 3. The nifedipine-treated animals went into anagen. Vehicle or other types of channel blocker-treated animals did not go into anagen, and other blockers had no phenotype, indicating a specific effect from nifedipine.

While L type channels are most often found in skeletal muscle, bone, cardiac myocytes, neuronal cell bodies, dendrites and endocrinal cells, they have also been localized to the skin. Of the four different types of L type channels, $Ca_v1.1$ (CACNA1S), $Ca_v1.2$ (CACNA1C), $Ca_v1.3$ (CACNA1D), $Ca_v1.4$ (CACNA1F) (Catteral et al, 2005). $Ca_v1.2$ is the only L type channel known that is expressed in the skin (mouse genome informatics; Denda et al, 2006). This suggests that $Ca_v1.2$ can contribute to hair cycle regulation in mouse skin.

Example 2

Figure 2:
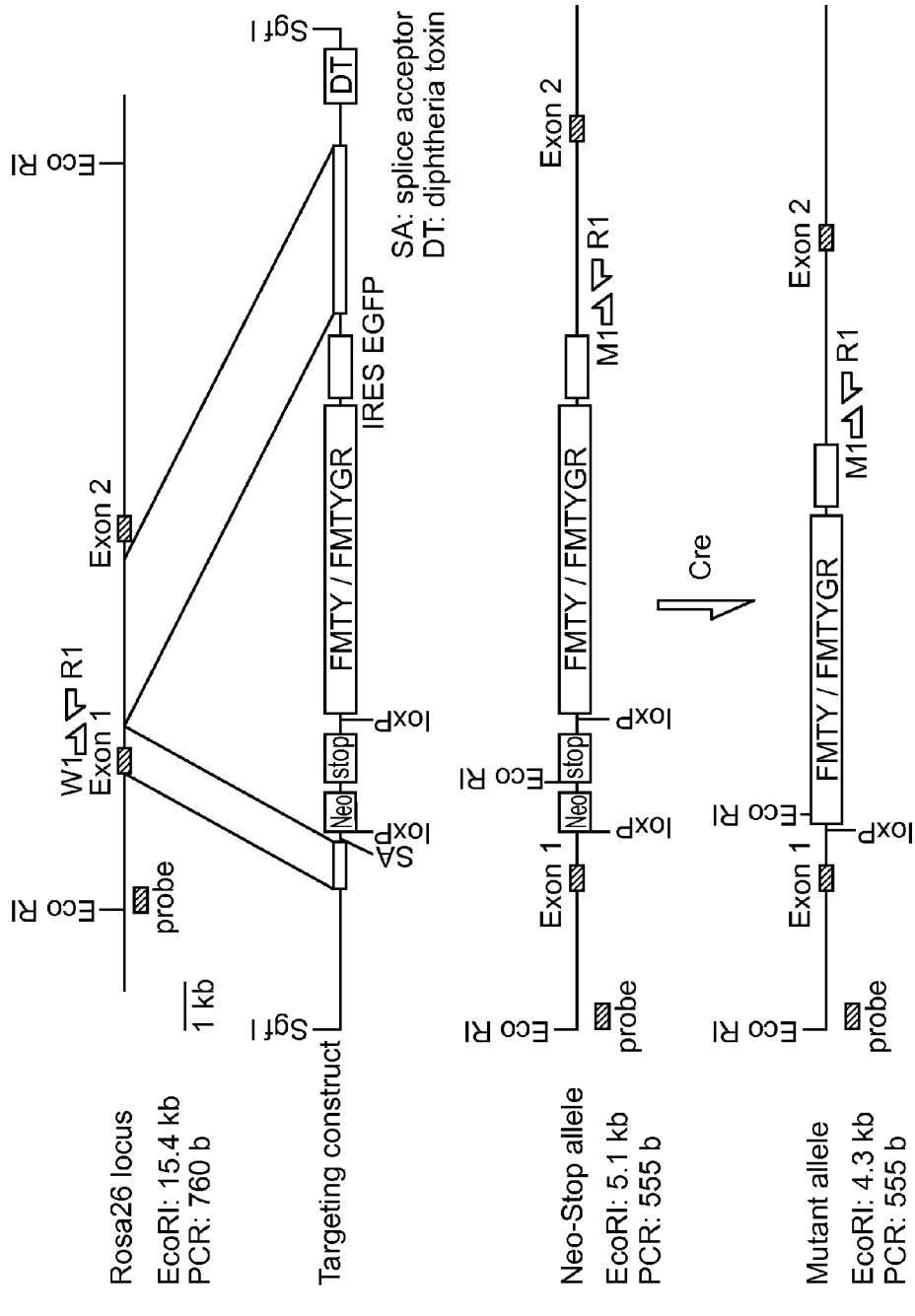
FIG. 2. Timothy syndrome targeting strategy.

To understand the role of Cav1.2 in hair cycling, we first observed Timothy Syndrome (TS) mice. Overexpression of this mutant channel is established by the removal of STOP codon (FIG. 2). Homozygous mice (TSfx/fx; K15CrePR) that are treated with RU486 demonstrate late entry to anagen by 5-8 days (n=6). H and E staining of the skin sections showed telogen hair follicles in TS mice compared to anagen hair follicles in the control mice. Nfatc1 staining of TS skin showed nuclear staining in the bulge stem cells indicating quiescence. Skin from control mice showed cytoplasmic Nfatc1 staining.

BrdU pulse chase experiments were performed, and it was observed that almost no BrdU incorporation was observed in TS mutant bulge, although BrdU incorporation was observed in the bulge and hair germ of control hair follicles. These results show that overexpression of TS mutant channel in the bulge stem cells in the skin inhibit anagen and extend quiescence. TS mutation represents the open state of the channel. To further explore the effect we observed the closed and inactivated states of the channel.

Loss of function mutation of this channel entails a removal of exon 13 and 14 of Cav 1.2 gene (FIG. 1). This mutation removes the pore region of the channel and does not let any calcium influx into the cell. Cav fx/- mice were crossed to K15CrePR animals to remove the pore region of the channel in the bulge stem cells. RU486 treatment of Cav fx/-; K15CrePR allowed the removal of the pore region. When we observed these mice for hair cycling defects, we saw that they went into anagen 6-8 later then their control littermates (n=15) (FIG. 3). H and E staining of the skin sections showed telogen hair follicles in mutant mice compared to anagen hair follicles in the control mice. Nfatc1 staining showed nuclear staining in mutant bulge cells. This data shows that removal of the pore of Cav1.2 has the same phenotype as TS mutant, extending quiescence. Loss of function mutation, which represents the closed state of this channel, results in the same phenotype as the open state of the channel.

Figure 5:
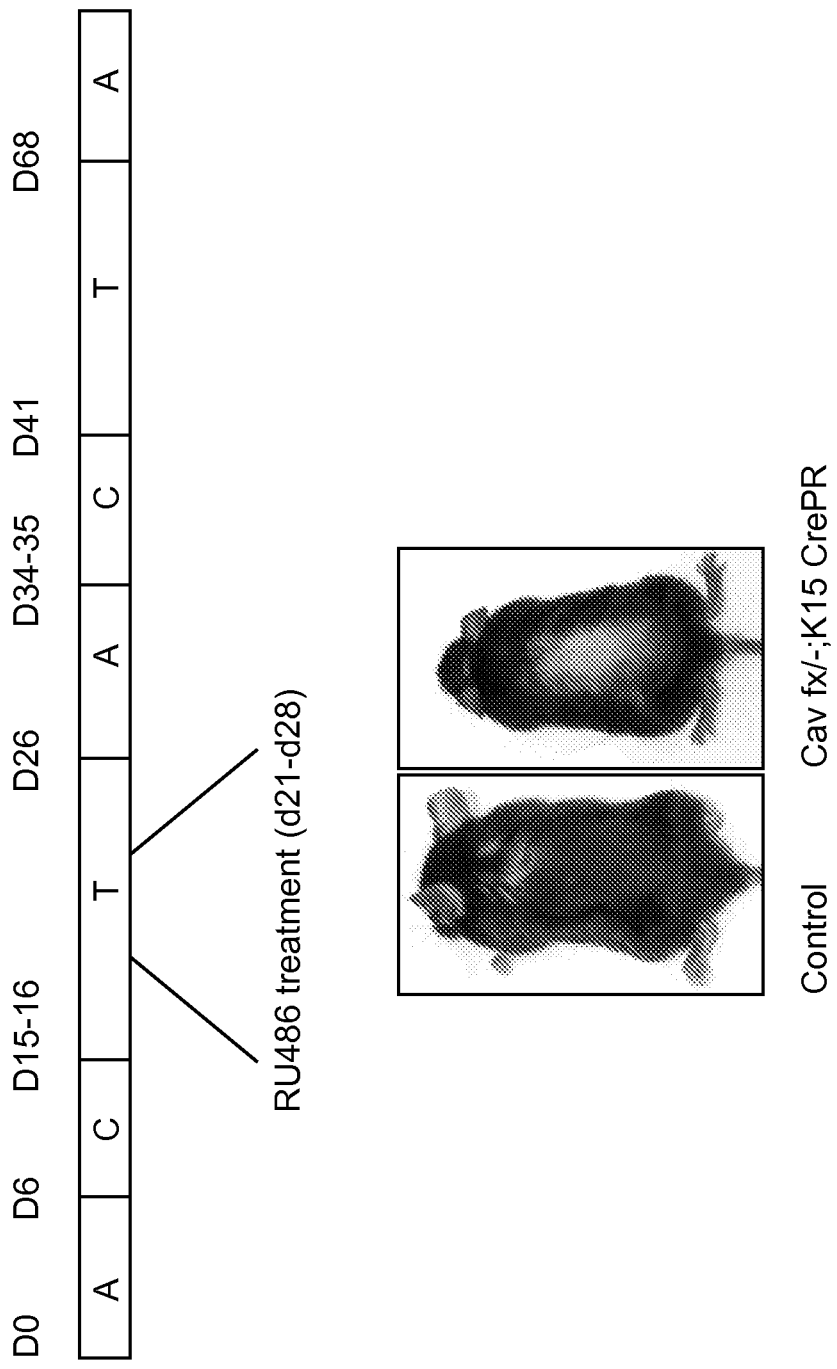
FIG. 5. Nifedipine causes precocious entry into anagen.
Figure 6:
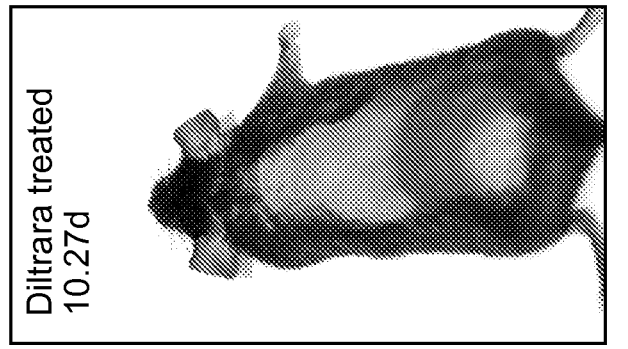
FIG. 6. Verapamil and Diltiazem cause precocious entry into anagen.
Figure 6:
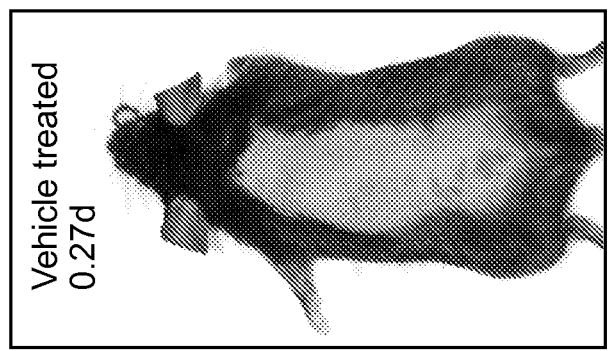
Figure 6:
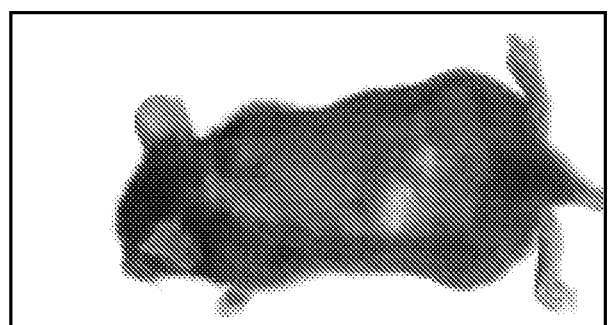
Figure 6:
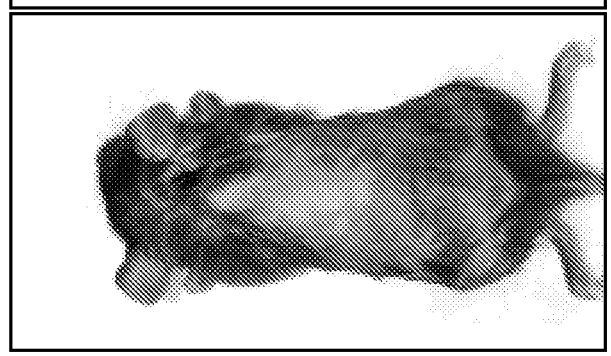

We performed a small molecule screen to find out if any of the available calcium blockers affected hair follicle cycling. Indeed, L type channel blocker Nifedipine caused a precocious entry to anagen (n=10). Other L-type channel blockers Verapamil and Diltiazem showed the same results (FIG. 5). Because Verapamil was the most potent, we used it for analysis.

Verapamil treatment of wild type mice between the days of 21 and 28 (first telogen) caused early anagen by 5-7 days in treated mice (n=8). H and E staining of the skin sections showed anagen hair follicles in drug treated mice compared to telogen hair follicles in the control mice. Nfatc1 staining of treated versus non-treated skin demonstrated that they both have Nfatc1 in the nucleus although the treated skin was already in anagen. These results show that Verapamil treatment of skin causes early entry to anagen but this effect is not mediated through repression of nuclear Nfatc1.

To understand if Verapamil is truly working on bulge stem cells, we drug treated Cav fx/-; K15 CrePR animals that were also RU486 treated. Drug treated mutant mice go into anagen 2-4 days later than their wild type littermates, suggesting that Verapamil treatment affects bulge stem cells. H and E staining of skin sections from treated mice showed anagen hair follicles compared to control skin with telogen hair follicles. Nfatc1 staining show nuclear staining in control bulge cells compared to cytoplasmic staining in mutant drug treated bulge cells.

Example 3

Figure 7:
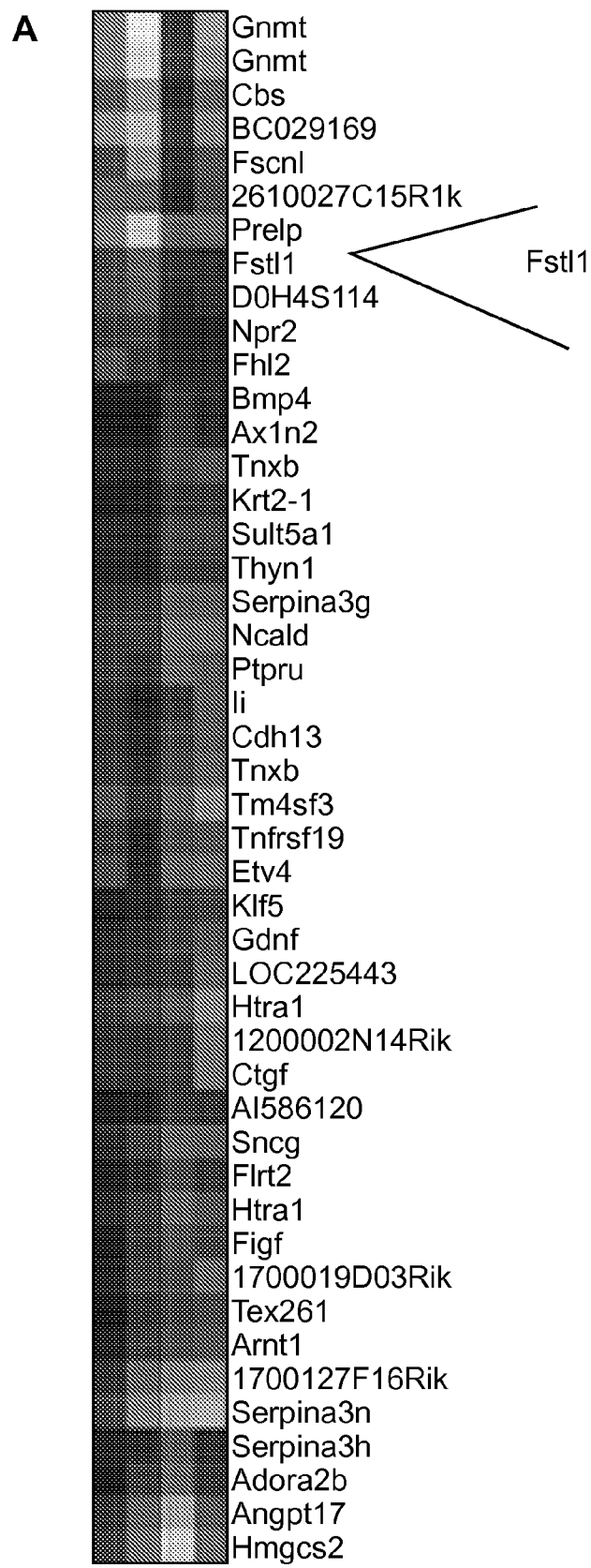
FIGS. 7A-7E. FSTL1 is downstream of Cav 1.2.
Figure 7:
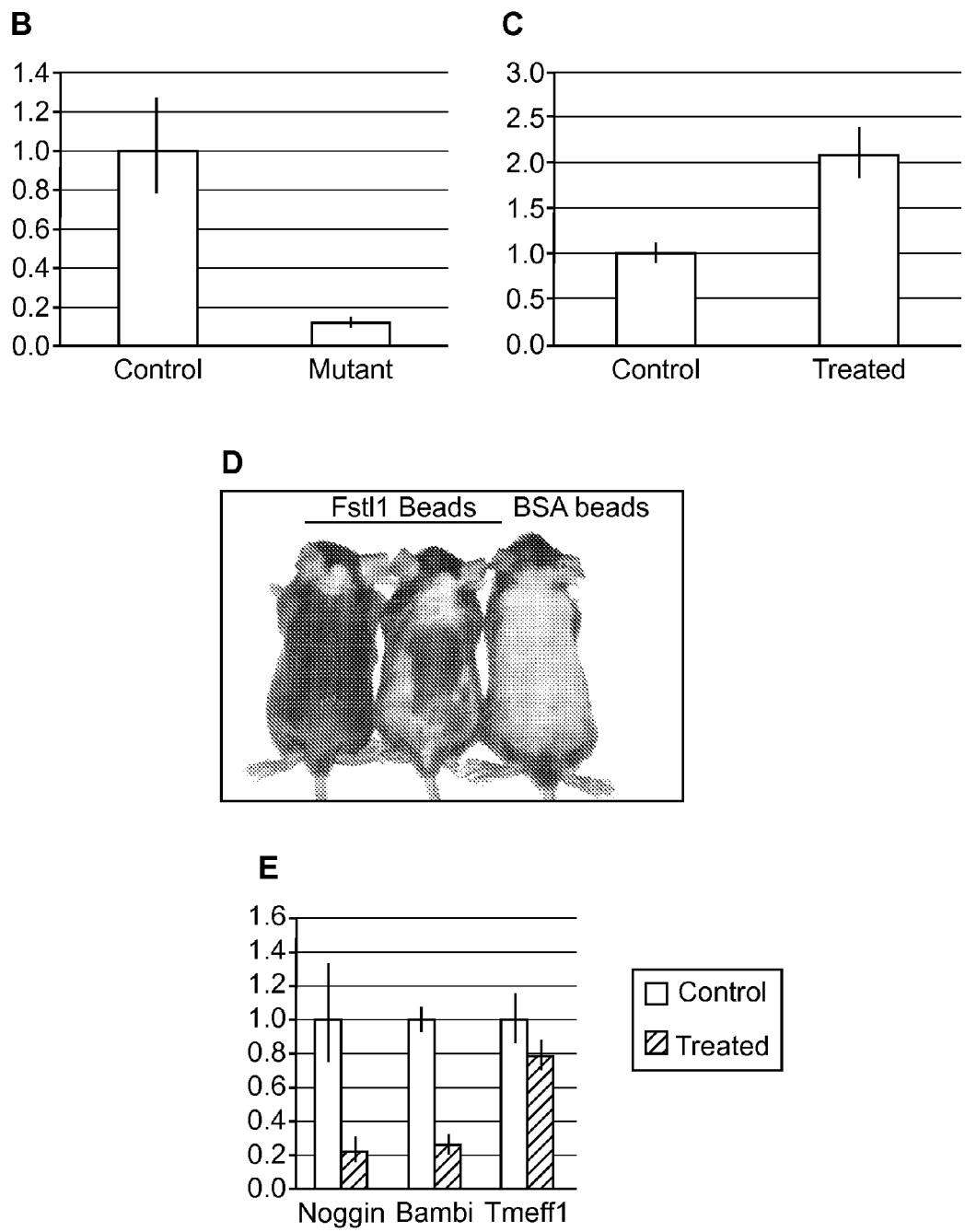

To understand the mechanism behind Cav 1.2 action, we performed microarray analysis on Verapamil treated, loss of function mutant and control bulge cells (FIG. 7A). We looked for genes that were upregulated/downregulated in mutant bulge cells that were downregulated/upregulated in treated bulge cells. Out of those, the gene Follistatin like 1 (Fstl1) stood out. Fstl1 is a secreted glycoprotein that inhibits BMP signaling in lung and ureter development. RT-PCR results showed that Fstl1 is downregulated in mutant bulge stem cells compared to control bulge cells (FIG. 7B) and upregulated in verapamil treated bulge stem cells compared to control bulge stem cells (FIG. 7C).

To understand the effect of Fstl1 on hair cycling, we subcutaneously injected two different doses of Fstl1 protein (4 µg and 2 µg) soaked beads to Day 21-22 mice. In 2 to 4 days, these mice went into anagen (n=8, FIG. 7D). Half dose caused only partial entry to anagen. BSA injected control animals did not go into anagen.

There are other BMP inhibitors that are known to affect hair cycling. Noggin and Bambi are downregulated in Verapamil treated bulge stem cells. Tmeff1 expression does not change much in treated bulge stem cells compared to control bulge stem cells (FIG. 7E). This data indicates that Cav1.2 is upstream of Fstl1 only and does not upregulate other BMP inhibitors.

What is claimed is:

1. A method for treating skin, scalp or hair comprising:
applying to skin, scalp or hair of an individual a composition comprising:
an effective dose of an agent to promote anagen phase of the hair cycle, where the agent is follistatin-like 1 protein; and a cosmetically acceptable vehicle.

2. The method of claim 1, wherein the individual is a human.

3. The method of claim 2, wherein the individual suffers from alopecia.

4. The method of claim 3, wherein the alopecia is androgenic alopecia.

5. The method of claim 1, wherein the composition further comprises verapamil combined with the follistatin-like 1 protein.

6. The method of claim 1, wherein the composition further comprises a penetration enhancer.

* * * * *